(12) United States Patent
Popovic et al.

(10) Patent No.: US 11,013,480 B2
(45) Date of Patent: May 25, 2021

(54) C-ARM TRAJECTORY PLANNING FOR OPTIMAL IMAGE ACQUISITION IN ENDOSCOPIC SURGERY (71) Applicant: KONINKLIJKE PHILIPS N.V., Eindhoven (NL)

(72) Inventors: Aleksandra Popovic, New York, NY (US); Haytham Elhawary, New York, NY (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1345 days.

(21) Appl. No.: 14/409,366

(22) PCT Filed: Jun. 17, 2013

(86) PCT No.: PCT/IB2013/054935
§ 371 (c)(1),
(2) Date: Dec. 18, 2014

(87) PCT Pub. No.: WO2014/001948
PCT Pub. Date: Jan. 3, 2014

(65) Prior Publication Data
US 2015/0190204 A1 Jul. 9, 2015

Related U.S. Application Data (60) Provisional application No. 61/665,356, filed on Jun. 28, 2012.

(51) Int. Cl.
A61B 6/00 (2006.01)
A61B 6/10 (2006.01)
(Continued)

(52) U.S. Cl.
CPC .......... *A61B 6/469* (2013.01); *A61B 1/00149* (2013.01); *A61B 1/04* (2013.01);
(Continued)

(58) Field of Classification Search
CPC ....... A61B 6/4441; A61B 6/466; A61B 6/481; A61B 6/504; A61B 6/547; A61B 6/5247
See application file for complete search history.

(56) References Cited

U.S. PATENT DOCUMENTS 5,485,502 A * 1/1996 Hinton .................. A61B 6/102
250/363.01
6,574,493 B2 6/2003 Rasche et al.
(Continued)

FOREIGN PATENT DOCUMENTS

JP 2009112388 A 5/2009

OTHER PUBLICATIONS

Maddux, J. et al, "Rotational angiography and 3D coronary modeling: revolutions in the cardiac cath lab", Medicamundi, Philips Medical Systems, Shelton, CT, US., vol. 47, No. 2, Aug. 1, 2003, pp. 8-14, XP002478297.

*Primary Examiner* — Joseph M Santos Rodriguez (57) ABSTRACT

An image acquisition system includes a first imaging modality device (102) configured to acquire images from a subject from a position. A second imaging modality device (124) is configured to acquire images of the subject from a plurality of poses selected based upon the position of the first imaging modality device and in accordance with criteria to provide a best pose or poses. A planning module (115) is stored in memory and is configured to determine at least one trajectory that permits the best pose or poses of the second imaging modality device to be achieved to acquire, in cooperation with the first imaging modality device, an image or images of the subject.

7 Claims, 6 Drawing Sheets (51) Int. Cl.
  *A61B 6/12* (2006.01)
  *A61B 6/02* (2006.01)
  *A61B 5/06* (2006.01)
  *A61B 34/20* (2016.01)
  *A61B 34/30* (2016.01)
  *A61B 34/10* (2016.01)
  *A61B 1/00* (2006.01)
  *A61B 1/04* (2006.01)
  *A61F 2/46* (2006.01)
  *A61B 90/00* (2016.01)

(52) U.S. Cl.
  CPC ............ *A61B 5/061* (2013.01); *A61B 6/027* (2013.01); *A61B 6/102* (2013.01); *A61B 6/107* (2013.01); *A61B 6/12* (2013.01); *A61B 6/4417* (2013.01); *A61B 6/4441* (2013.01); *A61B 6/488* (2013.01); *A61B 6/5229* (2013.01); *A61B 34/10* (2016.02); *A61B 34/20* (2016.02); *A61B 34/30* (2016.02); *A61B 1/0005* (2013.01); *A61B 2034/105* (2016.02); *A61B 2034/107* (2016.02); *A61B 2034/301* (2016.02); *A61B 2090/365* (2016.02); *A61B 2090/376* (2016.02); *A61F 2/4609* (2013.01)

(56) References Cited

U.S. PATENT DOCUMENTS

| | | | |
|---|---|---|---|
| 7,403,591 | B2 | 7/2008 | Wink |
| 8,004,229 | B2* | 8/2011 | Nowlin ................. B25J 9/1682 318/568.2 |
| 2006/0241465 | A1* | 10/2006 | Huennekens ............ A61B 5/06 600/458 |
| 2007/0249911 | A1* | 10/2007 | Simon .................... G06Q 50/24 600/300 |
| 2008/0013692 | A1 | 1/2008 | Maschke |
| 2008/0033240 | A1 | 2/2008 | Hoffman |
| 2008/0171936 | A1* | 7/2008 | Homan ................ A61B 6/4441 600/424 |
| 2009/0005641 | A1 | 1/2009 | Fehre et al. |
| 2009/0234444 | A1 | 9/2009 | Maschke |
| 2009/0259230 | A1* | 10/2009 | Khadem ................ A61B 34/20 606/130 |
| 2009/0262886 | A1 | 10/2009 | Mollus |
| 2010/0027742 | A1 | 2/2010 | Movassaghi et al. |
| 2012/0294498 | A1 | 11/2012 | Popovic |

* cited by examiner

C-ARM TRAJECTORY PLANNING FOR OPTIMAL IMAGE ACQUISITION IN ENDOSCOPIC SURGERY

CROSS-REFERENCE TO PRIOR APPLICATIONS

This application is the U.S. National Phase application under 35 U.S.C. § 371 of International Application No. PCT/IB2013/054935, filed on Jun. 17, 2013, which claims the benefit of U.S. Provisional Patent Application No. 61/665,356, filed on Jun. 28, 2012. These applications are hereby incorporated by reference herein.

This disclosure relates to medical instruments and more particularly to systems and methods for coordinating image collection using different imaging modalities.

Rotational X-ray C-arms are used in various interventional and surgical suites to acquire two dimensional (2D) and three dimensional (3D) images of an anatomy of interest. C-arm trajectory planning methods perform optimization of X-ray acquisition parameters (e.g., angular positions of the C-arm) based on a desired view. The desired view is usually defined on 3D images of previously acquired X-rays without considering specificities of surgical setups, e.g., where an endoscope or other instrument is inserted into the patient (e.g., chest cavity for endoscopic cardiac surgery).

In endoscopic surgery, the following additional issues may occur in projection planning. A range of motion of the C-arm is reduced when the endoscope is inserted, and the object of interest can be occluded due to scattering caused by metallic materials of the endoscope, particularly if the endoscope is between an X-ray source and the object to be imaged (e.g., an artery). Removing the endoscope to perform the imaging disturbs the workflow, causing prolonged operation time, and, potentially, an exchange of equipment may be needed if sterility is compromised. These issues further complicate the difficult task of C-arm position planning.

In accordance with the present principles, systems and methods are provided for planning and coordinating image acquisition using different imaging modalities. In one embodiment, an image acquisition system includes a first imaging modality device configured to acquire images from a subject from a position. A second imaging modality device is configured to acquire images of the subject from a plurality of poses selected based upon the position of the first imaging modality device and in accordance with criteria to provide a best pose or poses. A planning module is stored in memory and is configured to determine at least one trajectory that permits the best pose or poses of the second imaging modality device to be achieved to acquire, in cooperation with the first imaging modality device, an image or images of the subject.

Another image acquisition system includes an endoscope configured for viewing an area of interest and having a position. An X-ray system has a source and detector configured on a C-arm. The C-arm has its motion controlled to acquire images of the subject by moving the C-arm to a plurality of poses. A planning module is stored in memory and is configured to provide a cooperative plan to employ the position of the endoscope and the poses of the C-arm to optimize a view for acquiring an image or images of the subject in accordance with criteria.

A method for multi-modal image acquisition includes acquiring a scout scan with a first imaging modality having a moving structure; computing a position of a second imaging modality with respect to the moving structure; selecting an area of interest in an image of the second imaging modality; computing an optimal acquisition pose or poses for the moving structure using optimization criteria to determine a best pose or poses for the area of interest; rendering the best pose or poses to provide an optimized plan using preoperative images prior to acquiring images with the first imaging modality; and acquiring the images of the area of interest with the first imaging modality in accordance with the optimized plan.

Another method for multi-modal image acquisition includes acquiring a scout scan with an X-ray system having a source and detector configured on a C-arm; computing an endoscope position with respect to the C-arm; selecting an area of interest in an endoscope image for X-ray imaging; computing an optimal rotational acquisition pose or poses for the C-arm using optimization criteria to determine a best pose or poses for the area of interest; rendering the best pose or poses to provide an optimized plan using preoperative images prior to acquiring X-ray images; and acquiring X-ray images of the area of interest in accordance with the optimized plan.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

In accordance with the present principles, systems and methods are provided for planning and coordinating image acquisition using different imaging modalities. In one embodiment, an imaging modality may include X-ray imaging. Angular positions of an X-ray source and an X-ray detector are planned based on a position of an intraoperative imaging device, such as an endoscope. An optimal image of an anatomy of interest is obtained by avoiding collision of the X-ray imaging system with the endoscope. This avoids occlusion of an object of interest caused by X-ray scattering from metallic portions of the endoscope, and permits identification of the object of interest from live endoscopic images (in addition to planning from, e.g., preoperative images). These embodiments include clinical cases where minimally invasive surgery is performed under both an X-ray C-arm and endoscopy guidance. However, other imaging modalities may be included and are contemplated by the present principles.

In another embodiment, a method for robotically controlling the endoscope to extend an imaging field of view is provided. Where the endoscope is controlled robotically, the position of the C-arm and the robot can be combined in the optimization criteria to avoid collision of the X-ray imaging system and the robot without compromising image quality.

One step in a planning workflow is acquisition of a scout scan. The scout scan is acquired from a manually selected position of the C-arm in a same manner performed in standard clinical practice. In a next step, a relative position of the endoscope with respect to preoperative 3D images and/or intraoperative rotational X-ray images is computed. Then, the user selects an area of interest in the endoscope images that needs to be visualized by X-ray C-arm acquisition. In one example, the area may include a coronary artery. The system then computes an optimal acquisition protocol (or a series of acquisition protocols, e.g., a script) for an optimal trajectory of the C-arm. The optimization criteria may include one or more of the following: avoid collision of endoscope with the source/detector; minimize occlusion of the area of interest by the endoscope, maximize a visible portion of the area of interest; minimize radiation dose, etc.

In one conventional mode of operation, a C-arm is used to acquire a number of discrete 2D X-ray images where every C-arm rotational position is planned by the operator (radiologist, cardiologist, etc.). In this mode, the acquisition time may be very long which can have a negative impact on overall workflow. If a contrast agent is used, e.g., during coronary bypass surgery, the contrast agent is injected for each of the images, increasing risk of complications associated with high contrast agent dose. In another conventional mode of operation, a C-arm is used in a continuous rotational mode. The operator plans a motion trajectory for the imaging system, and a full rotational scan is performed. In this mode, a plurality of images is acquired allowing 3D reconstruction. Also, contrast agent dose may be significantly reduced as the contrast injection can be provided only once. In a third conventional mode of operation, a C-arm is used in fully rotational mode allowing a complete 3D reconstruction. This mode is usually referred to as cone-beam computed tomography (CT).

It is acknowledged in practice that planning of the C-arm angulations in any of above mentioned modes is a difficult and tedious task. Numerous software tools have been implemented to allow planning of C-arm motion for optimal acquisition. Trajectory planning methods perform optimization of X-ray acquisition parameters (angular positions of C-arm) based on a desired view as defined on 3D images or previously acquired X-ray images without considering specificities of surgical setups where an endoscope is inserted into the patient (e.g. chest cavity for endoscopic cardiac surgery).

In accordance with the present principles, these and other imaging modes are coordinated between multiple modalities to ensure a best image or pose is achieved to provide optimal results. In one embodiment, as the endoscope is used as the main imaging modality, it would be of value to allow X-ray image acquisition to be driven from the endoscope images. This is particularly useful in many instances. E.g., in a special case of coronary bypass surgery where a new artery (bypass) is introduced into the body, to validate revascularization, a rotational scan of the new artery is performed. This cannot be done using preoperative images, as the artery is not present in those images.

It should be understood that the present invention will be described in terms of medical instruments; however, the teachings of the present invention are much broader and are applicable to any scanning or imaging instruments. In some embodiments, the present principles are employed in tracking or analyzing complex biological or mechanical systems. In particular, the present principles are applicable to internal tracking or imaging procedures of biological systems, to procedures in all areas of the body such as the lungs, gastro-intestinal tract, excretory organs, blood vessels, etc. The present embodiments illustratively focus on a combination of X-ray and endoscopy guidance; however, this combination is exemplary as other imaging modalities and combinations may be employed in accordance with the present principles.

The elements depicted in the FIGS. may be implemented in various combinations of hardware and software and provide functions which may be combined in a single element or multiple elements. The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Figure 1:
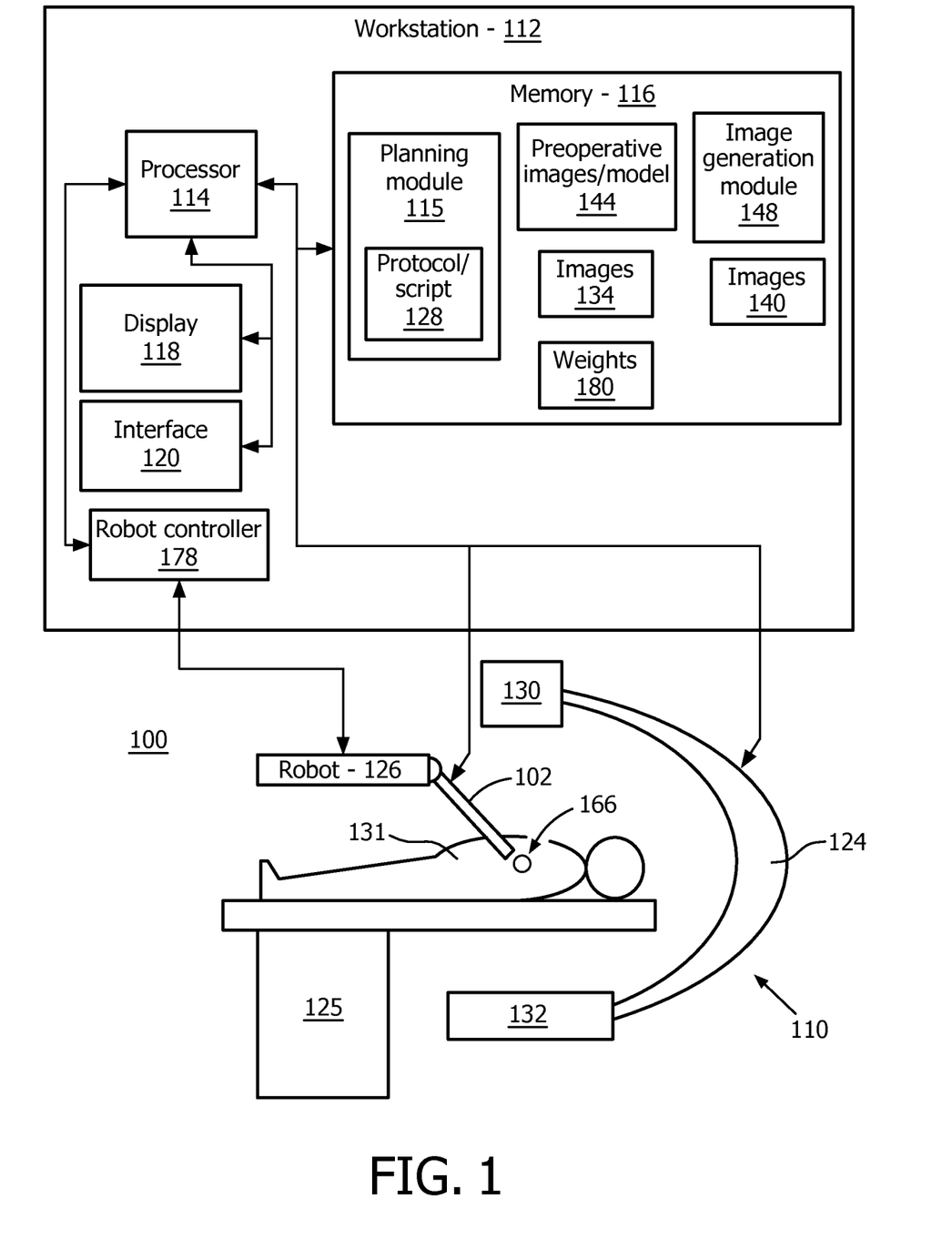
FIG. 1 is a block/flow diagram showing a hybrid imaging suite where multiple imaging modalities cooperate positionally to provide optimal images without interference between the modalities in accordance with one embodiment.

Referring now to the drawings in which like numerals represent the same or similar elements and initially to FIG. 1, a system 100 for cooperative imaging modalities is illustratively shown in accordance with one embodiment. System 100 is presented as an example of a minimally invasive cardiac surgery system. The present principles can be used for any type of procedure including an endoscope or other imaging instrument. Endoscopic procedures may include, e.g., prostatectomy, hysterectomy, arthroscopy, etc. System 100 shows an intraoperative setup for minimally invasive cardiac surgery in a hybrid operating room suite. System 100 may include a workstation or console 112 from which a procedure is supervised and/or managed. Workstation 112 preferably includes one or more processors 114 and memory 116 for storing programs and applications. Memory 116 may store a planning module 115 configured to coordinate or script actions by multiple devices or structures employed during a procedure. In one embodiment, the planning module 115 plans movements of one or more instruments or devices. In one embodiment, an X-ray C-arm 124, an endoscope (or other instrument), a robot 126 (optional) or other device or devices may all have their locations and motions scripted to cooperate in accordance with the present principles. A medical device or instrument 102 may be coupled to and guided by the robot 126 or may be employed manually without the robot 126. The medical device 102 may include a catheter, a guidewire, a probe, an endoscope, an electrode, a filter device, a balloon device, or other medical component, etc. In a particularly useful embodiment, the device 102 includes a scope or other imaging device to provide an imaging modality.

In one embodiment, workstation 112 includes an image generation module 148 configured to receive imaging signals from one or more of the imaging modalities, for imaging a subject or volume 131 (patient) illustratively depicted on an operating table 125. An image or images 134, 140, 144 of the patient, e.g., X-ray images, endoscope images, preoperative images, etc. can be displayed on a display device 118. Workstation 112 includes the display 118 for viewing internal images of the subject or volume (patient) 131 and may include the image as an overlay of images generated and/or registered by the image generation module 148 from multiple modalities, e.g., X-ray, endoscope, preoperative images, etc. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

The planning module 115 is employed for planning an X-ray C-arm acquisition protocol or script 128, in particular, angular positions of an X-ray source 130 and an X-ray detector 132 based on a position of the intraoperative endoscope or other device 102 (e.g., ultrasonic probe, etc.). An optimal image or images 134 of an anatomy or area of interest 166 are obtained by avoiding collision of an X-ray imaging system 110 with the endoscope 102, avoiding occlusion of the object of interest caused by X-ray scattering from the endoscope 102, and allowing identification of the area of interest 166, e.g., a heart from live endoscope images 140 (in addition to planning from preoperative images or model 144).

In one embodiment, the endoscope 102 is inserted into a chest cavity of the patient 131 to provide live images 140 of the area of interest 166 (e.g., the heart) during a procedure (e.g., bypass surgery). The patient is positioned on the operating table 125 and the endoscope 102 is inserted through the ribs into the chest cavity providing real-time visualization of the operating site. The C-arm 124 is positioned close to the patient (either mounted on the ceiling, the floor, etc. of the operating suite or configured to be mobile on wheels) so that the object of interest 166 (the heart) can be imaged to provide images 134.

Figure 2:
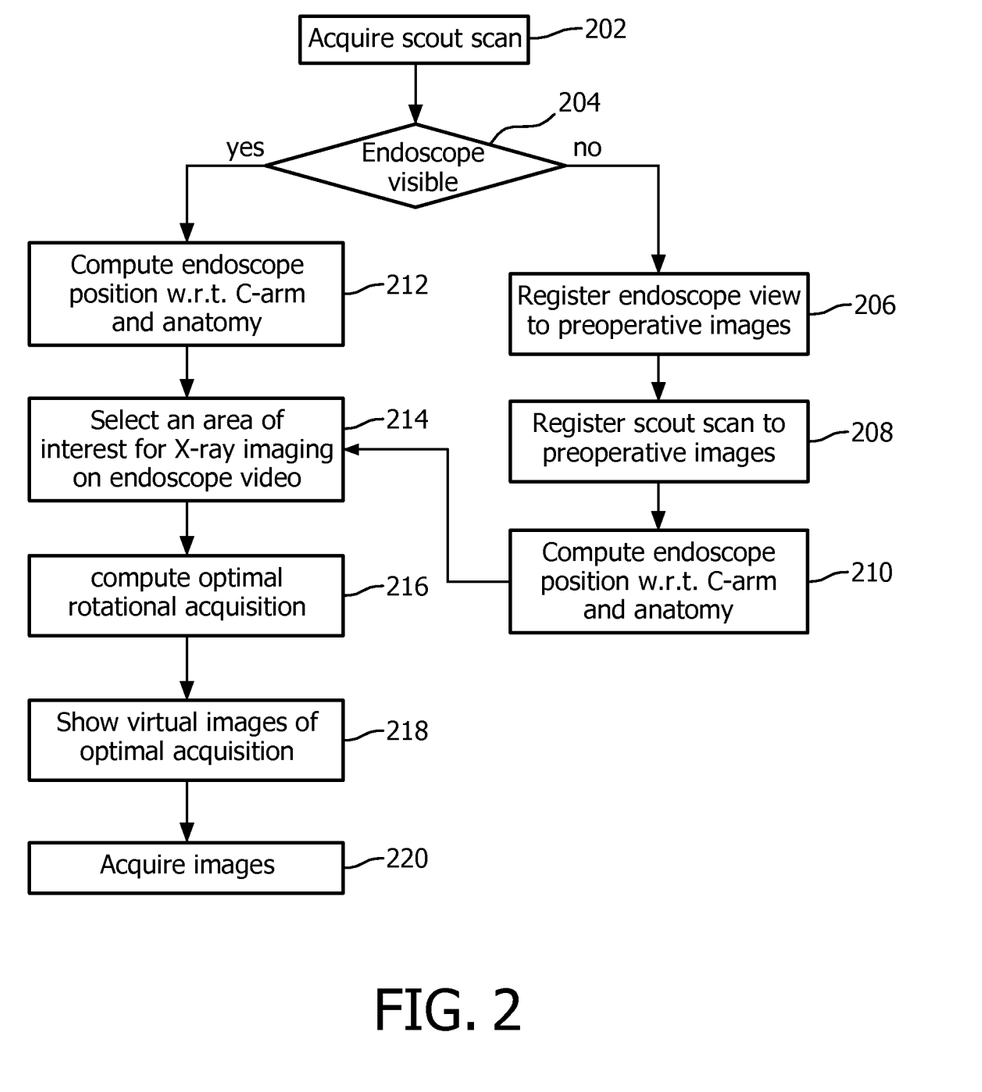
FIG. 2 is a flow diagram showing a method for multi-modal image acquisition in accordance with an illustrative embodiment.

Referring to FIG. 2, a method for planning a workflow is illustratively described in accordance with one embodiment. The planning workflow is performed using the planning module 115 (FIG. 1). In block 202, a scout scan is acquired from a manually selected position of the C-arm in a same manner as standard clinical practice. Depending on the selected projection view, the endoscope may or may not be visible in the scout scan. In block 204, a decision is made as to the visibility of the endoscope. If the endoscope is visible in the scout scan, the position of endoscope with respect to the C-arm can be found. To do this, a 3D model of an endoscope needs to be known prior to surgery. Further, the position of endoscope with respect to the anatomy can be found using 2D or 3D registration between X-ray and preoperative 3D imaging (CT, MRI) as known in art.

If the endoscope is not visible in the scout scan, the position of endoscope can be computed indirectly from preoperative 3D images, intraoperative X-ray images and/or endoscopy images. In block 206, a registration of endoscope to preoperative images can be performed by detecting point-pairs in endoscope images and preoperative images. Similarly, the endoscope images can be registered directly to X-ray images using the same method. Alternatively, the registration can be obtained by using other known methods.

In block 208, a registration of the endoscope image to the X-ray scout image and/or the preoperative 3D image is established. In block 210, a position of the endoscope with respect to the C-arm can be computed using known parameters of endoscope vision systems (camera focal length, pixel size, etc.). The program path continues with block 214. If in block 204, the endoscope is visible in the scout scan then a position of the endoscope with respect to the C-arm can be computed using known parameters of endoscope vision systems (camera focal length, pixel size, etc.) in block 212.

In block 214, a user selects an area of interest in the endoscope images that needs to be visualized by X-ray C-arm acquisition. For example, the area may include a coronary artery. In block 216, the system then computes an optimal acquisition protocol (or a series of acquisition protocols), in particular, the optimal trajectory of the C-arm. In block 218, virtual images of the optimal acquisition are shown to the user. In block 220, optimal images are acquired using the endoscope in relation to the C-arm.

Block 216 will be described in greater detail with continued reference to FIG. 1. A computation of optimal C-arm trajectory can be determined. The trajectory of the C-arm may be defined as any array of N consequent poses (e.g., described in three degrees-of-freedom of the arm), where N>0. Illustrative input parameters for the planning module 115 to determine a C-arm trajectory may include the following. Note that these parameters may be employed in sets of one or more input parameters including those mentioned here or others not mentioned. In one embodiment, a desired area of interest (e.g., artery) may be input by a user. This may include coordinates or other details learned from preoperative imaging or from the scout scan. Another input may include the position of the endoscope, which may be computed from a reference such as the C-arm or other structure, as described above.

A maximum allowed radiation dose may be provided as an input. This determines the amount of exposure time or number of images that can be collected. A preferred viewing direction may be input. Different users prefer different orientations and different patients may have different physiological constraints. For example, for imaging of coronary vasculature, some operators prefer a more caudal approach while some prefer more cranial angles. Different scan modes may be selected. This may be dependent on some of the other parameters (e.g., maximum dose) and the type of equipment being employed. Scan modes may include constant or intermittent image collection, number of angles, amount of exposure, time of exposure, etc. Detector orientation may also be an input parameter. Other input parameters, especially those that are employed to describe position or movements of the C-arm are also included.

Output parameters from the planning module 115 may include an array of poses of, e.g., the X-ray device 110 and a similar array of simulated images provided at the poses. The planning module 115 can generate any number of possible solutions and allow the user to select one or more positions or poses. Once the positions and locations of the C-arm are known as a function of time, optimization criteria are provided to determine acceptable positions and movement of the endoscope. Alternately, the positions of the endoscope may be employed as criteria for determining the poses of the C-arm 124 of the X-ray device 110.

The optimization criteria may illustratively include the following. Collisions between the endoscope and the source 130 and detector 132 of the C-arm need to be avoided. Since the C-arm positions are known, the positions of the endoscope 102 are controllable or vice versa. A comparison of position and movements can be determined by the planning module 115 over time to ensure that the same space is not occupied at the same time by multiple devices, and that movements between the endoscope 102 and the C-arm 124 will not cause a collision or even contact. Similarly, the positions are computed to: minimize occlusion of the area of interest 166 by the endoscope 102 relative to the source 130 and detector 132, and maximize a visible portion of the area of interest 166. In addition, radiation dose may be considered. Radiation dose may be determined as a function of position on the body of the patient. Too much radiation in a single area is to be avoided. The optimization criteria are employed to minimize radiation dose to all areas if possible.

In addition, the user can rank or weight 180 the criteria based on user preferences. For example, in some cases, occlusion may be more critical than maximization of the area of interest. Weights 180 may be scaled to prioritize equipment and may change as a function of time as different events occur during a procedure.

In one embodiment, the robot 126 may be employed to control the positions and movements of the endoscope 102. A robot controller 178 may be employed to control the robot 126 in accordance with the planning module 115. The planning module 115 may consider the robot 126 as a part of the endoscope 102, or the robot 126 may be considered separately as an independent object for which trajectories are considered to avoid collisions, etc.

Figure 3:
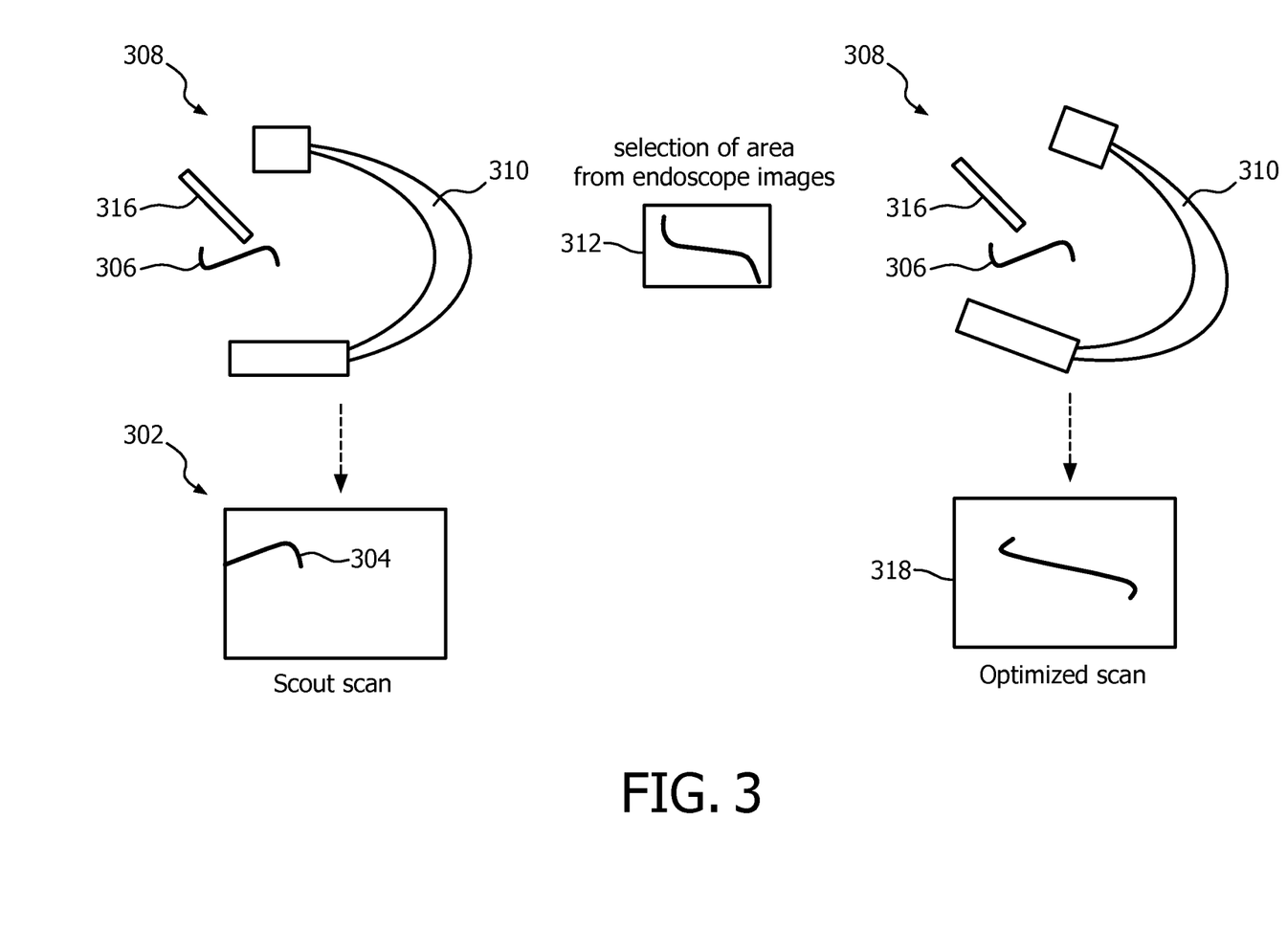
FIG. 3 is a diagram showing an optimization method for providing optimized X-ray scans in accordance with an illustrative embodiment.

Referring to FIG. 3, a schematic diagram shows an example of an optimization method to visualize an artery in X-ray images. In a scout scan 302, a part 304 of an artery 306 is visible due to a suboptimal pose or position 308 of a C-arm 310. Since the artery 306 is visible in an endoscope view 312 of an endoscope 316, the user selects the endoscopic view 312, and an optimization algorithm proposes a new pose 314 for the C-arm 310 to allow for a better visualization of the artery 306. Note that the new visualization may not be in the same plane as the endoscope view 312 (i.e., a different projection exists between the endoscope image 312 and an optimized scan 318); however, the entire area of interest is visible.

The optimization algorithm will be described for simplicity as a breadth-first search, but may be extended to any optimization scheme known in art. The planning module 115 (FIG. 1) computes all possible trajectories of the C-arm and generates simulated images from the preoperative 3D dataset (144) using methods known in the art. The planning module 115 (FIG. 1) additionally takes positions of the endoscope 316 into the account for the collision and occlusion detection using endoscope motion data. Further, models for X-ray scattering of metallic objects can be used to compute artifacts to provide for more accurate planning. For every possible computed image (correlated to the poses), the optimization criteria are computed, and the results are ranked (trajectories resulting in collision are rejected) based on a combination of parameters and ranking criteria provided by the user. A most optimal trajectory is presented to the user. Alternatively, the planning module 115 can present any number of trajectories optimized by different criteria.

While an endoscope's position may be accounted for directly as shown in FIG. 3, in other embodiments, the endoscope may be robotically controlled to extend imaging capabilities. In such embodiments, the robot's position is accounted for as well. Where the endoscope 316 is controlled robotically, the position of the C-arm 310 and robot can be combined in the optimization criteria to avoid collision of the X-ray imaging system and the robot without compromising image quality.

In embodiments where the anatomy of the subject is altered during the procedure, the preoperative images (144) may still be employed to provide proposed views from the X-rays. However, the images will not reflect the new anatomy since the new anatomy was not present during the acquisition of the preoperative images. This can be overcome by providing a model of a virtual anatomical portion and adding or subtracting the virtual anatomical portion to the preoperative images. In one example, an embodiment addresses a special case of imaging a bypass graft after the graft is placed on a diseased coronary artery. In this case, the particular anatomy is not present in the preoperative images. A model of the bypass artery can be artificially generated from endoscope images by manually delineating the visible portion of the artery and artificially adding the delineated shape to the 3D models from preoperative images by enforcing a user defined radius and shape (e.g., circular cross section). Although the precision of this approach will be lower than for arteries present in preoperative images, this method can yield a sufficiently adequate image acquisition protocol.

Figure 4:
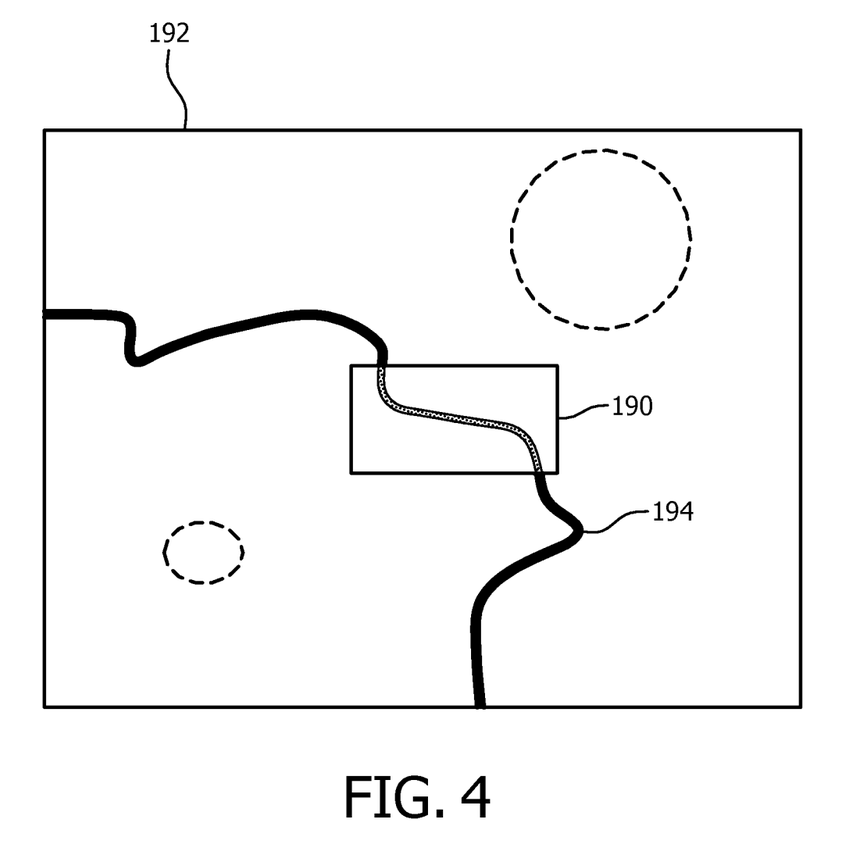
FIG. 4 is an illustrative image showing a live endoscopic image overlaid on an X-ray image background to provide an improved view of an area of interest in accordance with an illustrative embodiment.

Referring to FIG. 4, a picture-in-picture visualization may be employed. In this embodiment, a position of an endoscope image plane relative to a scout X-ray image is computed as described above. The planning system 115 (FIG. 1) then computes a pose of the C-arm so that the imaging plane coincides with the imaging plane of endoscope. Since the endoscope will occlude that image, the system computes a new position of endoscope where the occlusion is minimal, or the endoscope is moved (which may be performed using the robot controller/control system 178 to move the robot 126 to a new position (FIG. 1)). After the X-ray image is acquired, the endoscope can be moved back to its original position (e.g., by the robot 126). As the result of this protocol, a picture-in-picture visualization showing live endoscope video 190 and an X-ray extension image 192 of a field of view can be presented to the user. The endoscopic video 190 may be shown against a still background image of the X-ray image 192 (and/or preoperative images) to provide a more complete image of the region of interest (e.g., an artery 194).

Figure 5A:
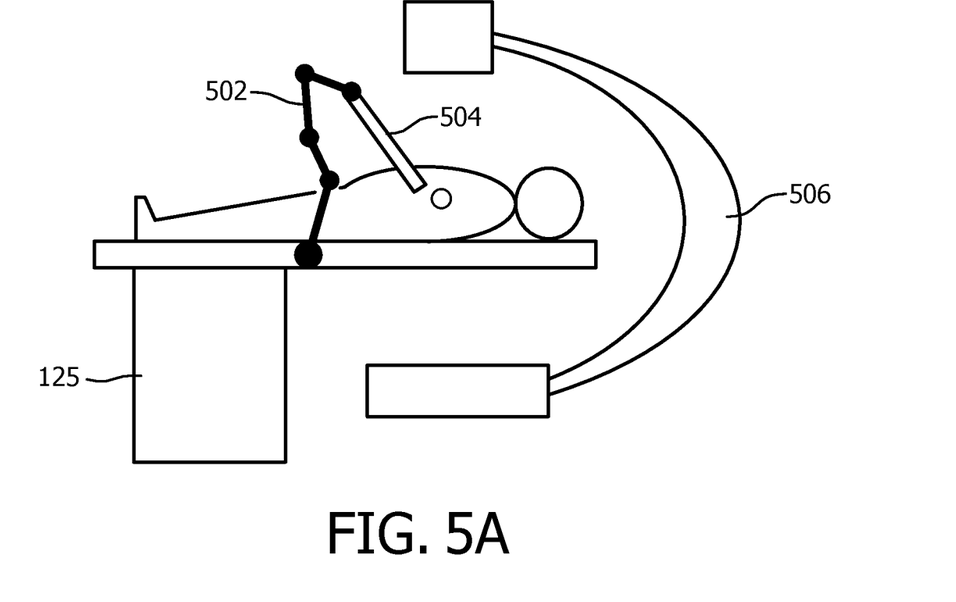
FIG. 5A is a diagram showing a C-arm in a first position and a robot system holding an endoscope in accordance with an illustrative embodiment.
Figure 5B:
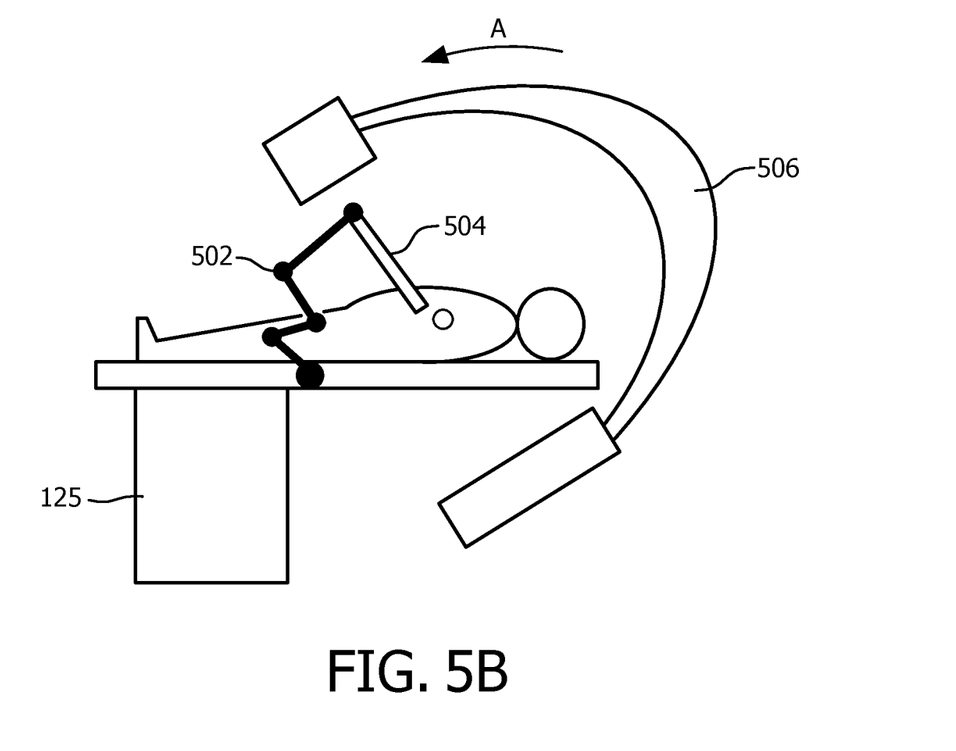
FIG. 5B is a diagram showing the C-arm in a second position and the robot system holding the endoscope in a same position but the robot system moving to avoid collision with the C-arm in accordance with an illustrative embodiment.

Referring to FIGS. 5A and 5B, a robotic system 502 holds an endoscope 504 in accordance with the present principles. The robotic system 502 needs to avoid collision with a C-arm 506. This can be done by using position information of the robotic system 502 to make sure its location is away from the optimized C-arm trajectory, without changing the endoscope's position or orientation.

In one embodiment, a special case exists where the endoscope 504 is being held by the robotic system 502 and is permitted to be timely and precisely removed from the X-ray field of view and then placed back to exactly the same location. Previous embodiments include optimization criteria to avoid collisions with the endoscope 504. In the case where the intervention is being performed with a robotic guided endoscope holder or robotic system 502, the optimization criteria may also need to include the presence of the robotic system 502. This can be solved by including the robot position information in the C-arm optimization algorithm, or if the robot system 502 has redundant kinematics, it can be moved in a way so as to avoid the new positions of the C-arm 506 without changing the orientation and position of the endoscope.

To include the robot position in the C-arm protocol optimization algorithm, the robot system 502 includes a coordinate frame that can be registered with a coordinate frame the C-arm 506. Given that the endoscope 504 is already registered to the C-arm 506, and that the robot system 502 is attached in a known way to the endoscope 504, the registration between coordinate systems can be performed with standard robotic methods (e.g., transformations that permit registration). Once this is done, a robot kinematic model and joint positions of the robot system 502 can be used to compute the location of the entire robot system 502 in the C-arm coordinate frame. This information can be included in the C-arm optimization scheme.

To use the robot redundant kinematics to ensure there is no collision with the C-arm 506, the C-arm positions calculated using the optimization protocols would have to be converted into the robotic coordinate reference frame. Once this is done (with a similar method as described above), the robot kinematic model can compute positions of the robot system 502, such that without changing the endoscope position or orientation can move the robot system 502 away from the trajectory of the C-arm 506. This can be illustratively seen in comparing FIG. 5A to FIG. 5B. FIG. 5A shows the robotic system 502 relative to a first position or pose of the C-arm 506. FIG. 5B shows a new position for the C-arm 506 (e.g., rotated in a direction of arrow "A"). The robotic system 502 has taken on a new configuration that moves out of the way of the C-arm 506; however, the endoscope 504 in both FIG. 5A and FIG. 5B remains in the same place despite the movement of the robotic system 502 holding the endoscope 504.

The present principles provide registration between coordinate systems of different imaging modality types to provide a plan for moving imaging hardware to provide the optimal view angles, avoid collisions and provide best results. The selection of target points on the endoscope image and the motion of the C-arm according to some optimized criteria improve the visualization of the selected target anatomy. The present principles can be employed in any operating room environment and are particularly useful in hybrid operating rooms where endoscopes and C-arms are employed. Procedures where the present principles are of particular use include a variety of cardiac, oncology, neurosurgery or other procedures. The present principles may also be extended to rooms where a mobile C-arm is used together with an endoscope and other scenarios.

Figure 6:
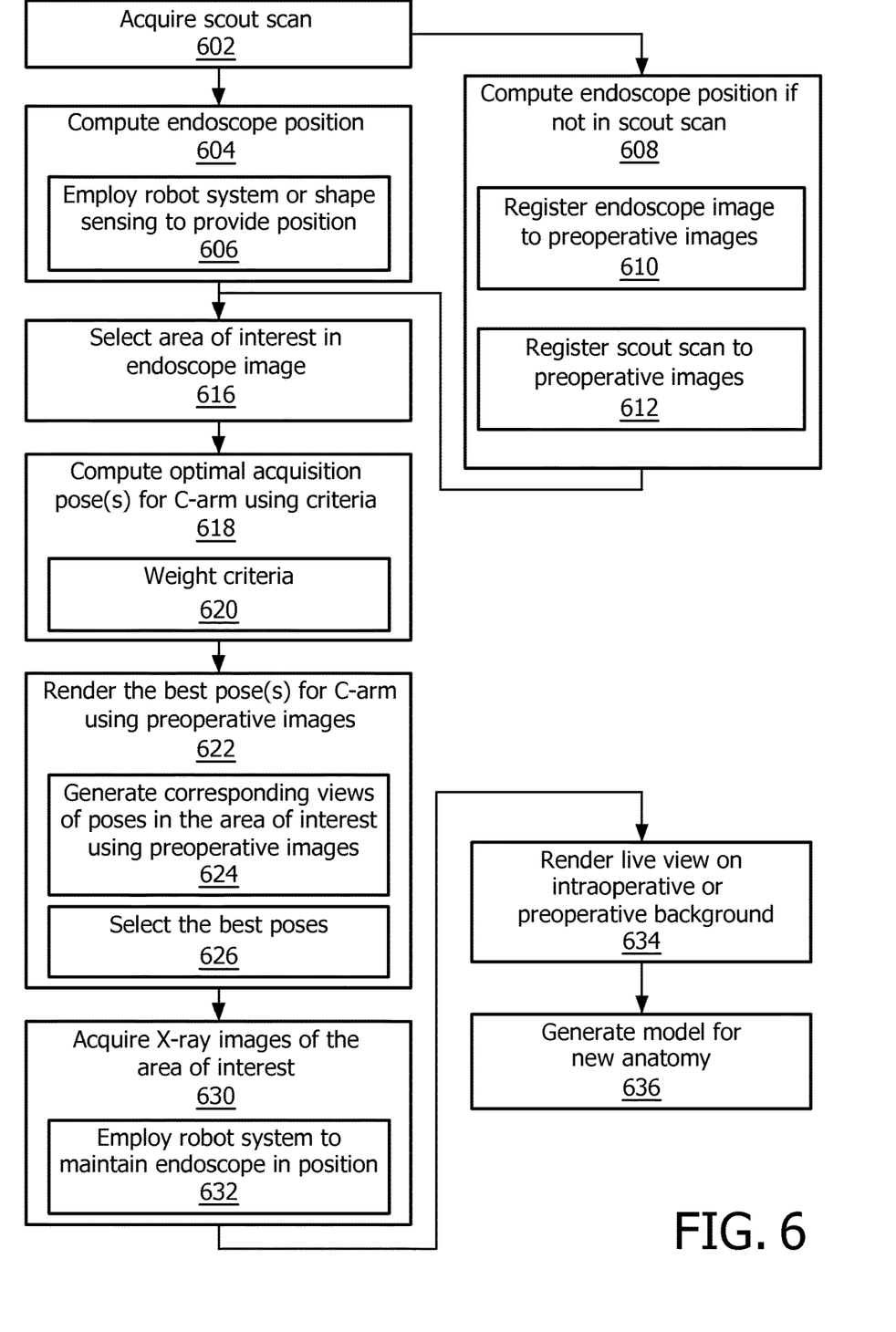
FIG. 6 is a flow diagram showing another method for cooperative multi-modal image acquisition in accordance with an illustrative embodiment.

Referring to FIG. 6, a method for multi-modality imaging acquisition is illustratively depicted in accordance with exemplary embodiments. In block 602, a scout scan is acquired with an X-ray system (or other imaging system) having a source and detector configured on a C-arm. In block 604, an endoscope position (or position of another imaging modality) is computed with respect to the C-arm. This is may be performed easily when the scout scan includes at least a portion of the endoscope, since the endoscope's position should be known. In one embodiment, a position(s) of the endoscope may be determined using a robot system, or a sensor system such as a fiber optic shape sensing system, etc. in block 606.

In the event that the endoscope image is not present in the scout scan, the endoscope position needs to be computed by another method in block 608. In block 610, a view of the endoscope is registered with the preoperative images. In block 612, the scout scan is registered to the preoperative images to compute the endoscope position with respect to the C-arm.

In block 616, an area of interest is selected in an endoscope image for X-ray imaging. In block 618, an optimal rotational acquisition pose or poses is/are computed for the C-arm using optimization criteria to determine a best pose or poses for the area of interest. The optimization criteria may include one or more of: avoiding collision between the endoscope and the C-arm; avoiding occlusion of the area of interest, visualizing the area of interest and/or controlling radiation dosage. Other criteria are also contemplated. In block 620, the optimization criteria may be weighted to prioritize the optimization criteria. This may include assigning a numerical weight or addressing the criteria in a given order to produce a desired result.

In block 622, images of the best pose or poses are rendered on a display to permit a user to select pose positions to optimize a plan. The pose images may include preoperative images taken prior to acquiring the X-ray images. This may include employing a plurality of positions of the C-arm to generate corresponding views of the area of interest from the preoperative images in block 624, and selecting the best pose or poses by viewing the preoperative images in block 626. The best poses may include the poses that provide a full view of the area of interest, have low X-ray scatter, provide an unoccluded view of the area of interest, reduce radiation dose, etc.

In block 630, the X-ray images of the area of interest are acquired in accordance with the optimized plan. The optimization plan may be implemented by controlling the manner and positions of the imaging modalities. In block 632, during image acquisition, a robot system is configured to maintain a position of the endoscope, and the robot system moves or changes its position to avoid collision with the C-arm while maintaining the position of the endoscope.

In block 634, a live endoscope view may be rendered on a corresponding position in an X-ray image background to provide a more complete image for the user. In block 636, an image model or other rendering may be generated of an anatomy change and added to the preoperative images to account for anatomical changes made in the area of interest after the preoperative images have been acquired. This model may be drawn by the physician or otherwise entered into the preoperative 3D model.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for C-arm trajectory planning for optimal image acquisition in endoscopic surgery (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. An image acquisition system, comprising:
an endoscope configured to acquire images of an area of interest of a subject and having a position;
an X-ray system having a source and detector configured on a C-arm, the C-arm having controlled motion to acquire images of the area of interest by moving the C-arm to a plurality of poses; and
a planning module stored in memory and, in connection with a processor, configured to provide a cooperative plan in accordance with optimization criteria to: employ the position of the endoscope and the poses of the C-arm to optimize a view for acquiring an image or images of the subject; and minimize or avoid occlusion of an area of interest in the subject.

2. The image acquisition system as recited in claim 1, wherein the optimization criteria further comprises one or more of: collision avoidance between the endoscope and the C-arm; at least one of a visualization of the area of interest and radiation dosage control.

3. The image acquisition system as recited in claim 2, wherein the optimization are weighted to prioritize the optimization criteria.

4. The image acquisition system as recited in claim 1, further comprising a robot configured to move and obtain the position of the endoscope.

5. The image acquisition system as recited in claim 4, wherein the robot is configured to maintain a position of the endoscope, and the cooperative plan provides motion information to a robot controller such that the robot moves to avoid collision with the C-arm, when moved, while maintaining the position of the endoscope.

6. The image acquisition system as recited in claim 4, wherein the cooperative plan includes a script for moving the C-arm during a procedure wherein the cooperative plan is derived using preoperative images.

7. The image acquisition system as recited in claim 1, wherein the images acquired by the endoscope are used to select the area of interest.

* * * * *